United States Patent [19]

Novick

[11] Patent Number: 5,817,956

[45] Date of Patent: Oct. 6, 1998

[54] METHOD FOR DETERMINING AEROSOL PARTICLE SIZE DEVICE FOR DETERMINING AEROSOL PARTICLE SIZE

[75] Inventor: Vincent J. Novick, Downers Grove, Ill.

[73] Assignee: The United States of America as represented by the United States Department of Energy, Washington, D.C.

[21] Appl. No.: 982,891

[22] Filed: Dec. 2, 1997

[51] Int. Cl.⁶ ................................................. G01N 15/02
[52] U.S. Cl. .......................................................... 73/865.5
[58] Field of Search ........................... 73/28.01, 28.03, 73/865.5; 55/270

[56] References Cited

U.S. PATENT DOCUMENTS 4,117,715 10/1978 Hoenig .................................. 73/28.03
4,742,718 5/1988 Jimbo ........................................ 73/73
5,369,981 12/1994 Merz et al. ............................ 73/28.01

*Primary Examiner*—Robert Raevis
*Attorney, Agent, or Firm*—Bradley W. Smith; Thomas G. Anderson; William R. Moser

[57] ABSTRACT

A method for determining the mass median diameter D of particles contained in a fluid is provided wherein the data of the mass of a pre-exposed and then a post-exposed filter is mathematically combined with data concerning the pressure differential across the same filter before and then after exposure to a particle-laden stream. A device for measuring particle size is also provided wherein the device utilizes the above-method for mathematically combining the easily quantifiable data.

24 Claims, 2 Drawing Sheets

METHOD FOR DETERMINING AEROSOL PARTICLE SIZE DEVICE FOR DETERMINING AEROSOL PARTICLE SIZE

BACKGROUND OF THE INVENTION

1. Field of the Invention

This invention relates to a method and device for determining aerosol particle size, and more specifically this invention relates to a method and device for determining aerosol particle size based on certain filter loading parameters.

2. Background of the Invention

The problems associated with the presence of particulates in air due to combustion and other activities continues to increase. Fine particles, i.e., particles at or below 2.5 microns ($\mu$m) in diameter are the most damaging to health inasmuch as they penetrate and remain in the deepest lung passages. The U.S. EPA estimates that approximately 15,000 premature deaths occur each year as a result of fine particle respiration.

Recently, the EPA promulgated annual limits of 15 micrograms of fine particles per cubic meter. Implementation of these regulations requires the availability of dependable and affordable particle size measuring methods and devices.

Particle size measurement is also useful for monitoring industrial processes. For example, a change in operating conditions may cause a change in the diameter of the emitted aerosols.

Current means for measuring particle sizes in the critical range of 0.03 to 5 microns entails the use of very advanced and costly methods incorporating lasers and/or other complex equipment. For instance, the SMPS (Scanning Mobility Particle Sizer available from TSI, Minneapolis, Minn. costs $50,000 to $60,000, covers the range 0.01 to 1 microns, and uses a laser based system supplemented by an electrical mobility analyzer. This device analyzes the mobility of aerosol particles that have been electrostatically charged and then subjected to an electric field.

Another laser-based system, the LSXRRT, supplied by Particle Measuring Systems of Boulder, Colo. costs $42,000 and covers the 0.065 to 5 microns range. It operates at relatively low flow rates.

A need exists in the art for an inexpensive method and device to measure the size of small particles suspended in a fluid, particularly particles in the 0.03 to 5 $\mu$m diameter range. The method and device should be adaptable to on-line operations and to installation on mobile units.

SUMMARY OF THE INVENTION

It is an object of the invention to provide a method and a device for the measurement of the mass median diameter (MMD) of solid aerosol particles that overcomes many of the disadvantages of the prior art. MMD is defined as the diameter wherein half of the mass of the particles resides in particles with diameters above the MMD and the other half of the mass resides in particles with diameters below the MMD. A feature of this invention is that it relies on the measurement of the following easily quantified bulk physical quantities: mass of particles accumulated on a filter, pressure upstream and downstream from the filter, and velocity of fluid flow through the filter. An advantage of this method is that it can be used with a variety of widely available instruments.

Another object of this invention is to provide a method for the measurement of the mass median diameter of a variety of aerosol particles. A feature of the present invention is that it utilizes a measurement method that is not sensitive to the chemical composition of the particles to be measured. An advantage of the present invention is that it can be utilized in conjunction with a wide variety of aerosol particle shapes and carrier gases resulting from a variety of industrial processes.

Yet another object of the invention is to provide a method for the measurement of the mass median diameter of solid aerosol particles that can be utilized in conjunction with a myriad of industrial operations. A feature of the present invention is that it utilizes relatively inexpensive parts and equipment. An advantage of the present invention is that the devices can be mass-produced, inexpensively installed, and used by personnel having a wide variety of skills and backgrounds.

Still a further object of this invention is to provide a device for the measurement of the mass median diameter of solid aerosol particles in real time. A feature of the present invention is that it can easily be incorporated in commercially available real time aerosol mass monitors. An advantage of the present invention is that it provides in real time the mass loading, the mass concentration, and the aerosol mass median diameter, which are all quantities that can be used to monitor industrial processes in situ and for minimal capital outlay.

Briefly, the invention provides for a method for determining the mass median diameter D of particles contained in a fluid, the method comprising initially passing a fluid at a velocity V through a filter having an area A to determine an initial fluid pressure differential $\Delta P_0$ across said filter; contacting for a time t particles to said filter to retain said particles on said filter; determining the mass M of the retained particles; and, while passing the fluid at the same velocity V thorough the now-contacted filter, determining a second fluid pressure differential $\Delta P_t$ across said filter; whereby the mass median diameter D of the particles is determined by means of an equation relating D to $\Delta P_0$, $\Delta P_t$, A, V, and M.

The invention also provides a device for determining the mass median diameter D of particles contained in a fluid, comprising a conduit having a first end and a second end, wherein said first end is adapted to receive the fluid at a first pressure $P_{in}$ and wherein said second end is adapted to exhaust the fluid at a second pressure $P_{out}$; a filter having an area A inserted at a time t=0 between the first and second ends of said conduit, with the fluid flowing through the filter at a velocity V; pressure probes affixed at each end of the conduit and connected to means for determining a pressure differential $\Delta P_t = P_{in} - P_{out}$ at any time t; means for maintaining the flow of fluid through the conduit for a predetermined time t during which time a mass M of particles is collected by the filter; means for ensuring that the velocity through the filter at time t is again V; means for measuring the mass M collected between t=0 and t; and means for computing D by means of an equation relating D to $\Delta P_0$, $\Delta P_t$, A, V, and M.

These and other features and advantages of the invention will be apparent from the detailed description of the invention and from the claims.

BRIEF DESCRIPTION OF THE DRAWING

The invention together with the above and other objects and advantages will be best understood from the following detailed description of the preferred embodiment of the invention shown in the accompanying drawing, wherein:

FIG. 1 is a schematic depiction of an apparatus for measuring particle size according to the present invention; and FIG. 2 is a graph comparing certain particle diameters determined by different methods with the same diameters measured in accordance with the present invention.

DETAILED DESCRIPTION OF THE INVENTION

The invention measures the mass median diameter of aerosol particles entrained in a fluid (typically a gas). Under most circumstances, only a fraction of effluent from a given source will be diverted to the invented system and analyzed.

When particles collect on the surface of a filter, a change in pressure across the filter results. The inventor has devised a method and device for comparing this pressure change to the pressure change across a clean filter to determine the mass median diameter of the particles. Generally, as particles collect on a filter, the rate of the gas flow through the filter is reduced. To obtain a specific gas flow rate one must increase the pressure differential across the filter. The increase in the pressure differential is a sensitive function of the diameter and of the total mass of the solid particles accumulated on the filter. A measurement of the increase in the pressure differential and accumulated mass provides a reliable value of the mass median diameter of the accumulated particles.

As noted supra, the device provides, and in real time, mass loading, mass concentration, and aerosol mass median diameter associated with aerosol measurement processes. Mass loading is the mass collected on the filter per unit filter area; mass concentration is the mass of particles per unit volume of air so that Mass concentration =

$$\frac{\text{Mass Loading} \times \text{Area}}{\text{Volume flow rate through the filter} \times \text{Collection time}}.$$

Figure 1:
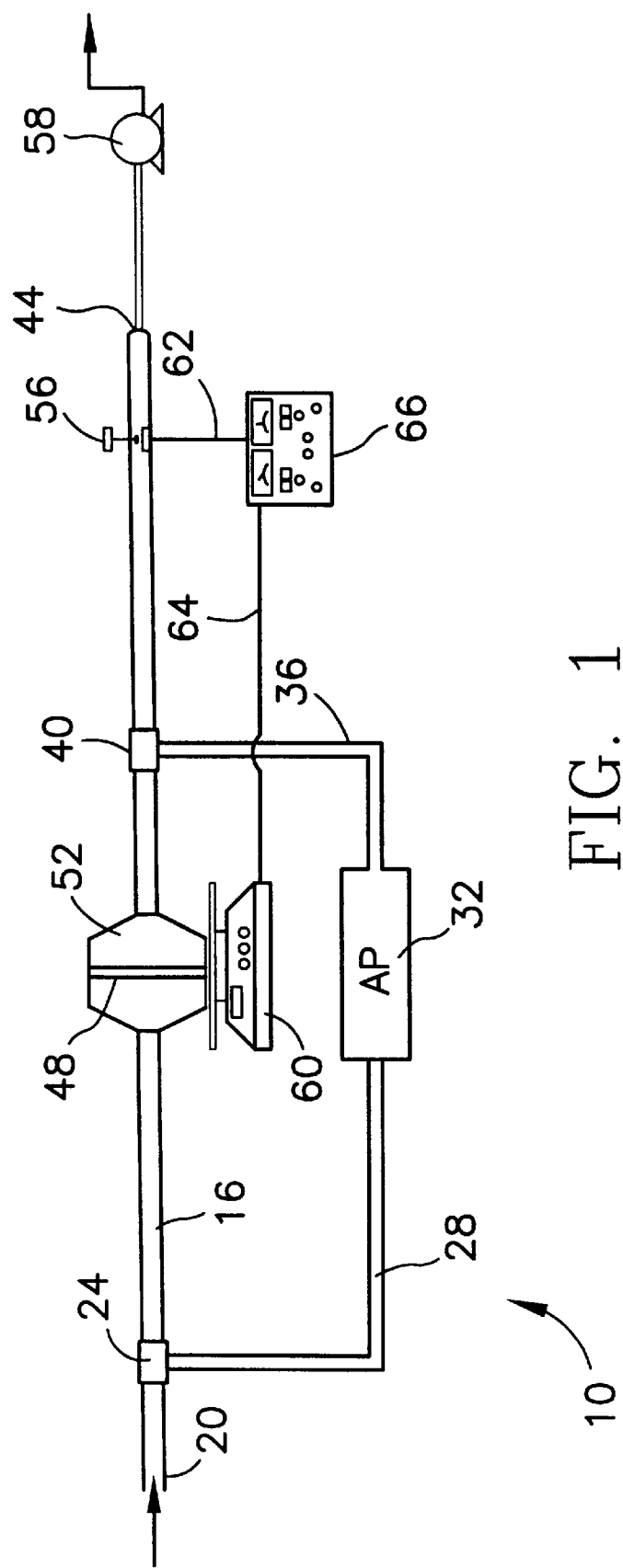

FIG. 1 illustrates a schematic embodiment of a system generally designated as 10) incorporating features of the present invention.

The gas containing the particles is admitted at an inlet end of the system, such as a first end 20 of a conduit 16. The gas passes through a filter 48, having a cross-sectional area A, at a velocity V. In situations involving pleated filters, such filters are generally situated so that a portion of its cross section is perpendicular to the laminar flow of the incoming gas.

After filtration, the gas, sans particles, ultimately exits at an outlet end 44 of the system.

The flow of gas through the system is maintained by a flow controller 56 and a vacuum pump 58 connected to the outlet end 44. Inasmuch as V=Q/A, wherein Q=volume flow, velocity can be controlled via hot wire anemometry or Q can be controlled via a laminar flow controller which measures heat loss or transfer. The pressure at the inlet end 20 and outlet end 44 is sampled by means of a first tee junction 24 and second tee junction 40. Means for supplying pre-filtered and post-filtered gas from the tee junctions 24 and 40 respectively to a pressure transducer 32 are provided. Specifically, lines 28 and 36 connect regions 24 and 40 respectively to a transducer 32 to measure the pressure difference between the probes 24 and 40. The transducer 32 is typically a capacitance manometer if an electronic readout is required. A water manometer can be used for manual calculations.

After a filter is inserted (time t=0), the pressure differential $\Delta P_0$ between the two ends is determined as is the velocity V of the gas. After a predetermined time t, during which an adequate mass of particles has accumulated on the filter, one ensures that the gas velocity is again V and then the pressure difference $\Delta P_t$ between the two ends is determined. The mass M of particles that has accumulated on tie filter is also measured, either in situ or by removing the filter. The mass median diameter D of the particles in the filter is obtained when the experimentally derived data is combined in equation 1 as follows:

$$D=a/(((\Delta P_t-\Delta P_0)A/VM)+b) \qquad \text{Equation 1}$$

Empirical studies conducted in situ determine a and b for the specific aerosol and filter types used by comparing the diameter predicted by the equation with the diameter measured by a completely different method. Stated differently, a and b can be determined empirically given values for D, $\Delta P_t$, $\Delta P_0$, A, V, and M, which are determined experimentally. It must be noted that a is not the same as the quantity that is often referred to as $k_1$ (i.e. filter resistance) nor is b the same quantity as $k_2$ (i.e. filter-cake resistance). Surprisingly and unexpectedly, experiments conducted at the inventor's laboratory indicate that for a wide variety of aerosols and filter types, an accuracy of at least 20 percent can be obtained when a is set at between 0.9 and 1.0, preferably at 0.95, and b is set at between $1\times10^5$ and $2\times10^5$, preferably at $1.6\times10^5$. Generally, $\Delta P_t$ increases as the MMD decreases. This is due to tighter packing on the filter surface associated with smaller particles. Equation 1 allows one to determine MMD whenever a measurable mass M causes a measurable increase in the pressure differential across the filter.

More generally, as long as one remains in the region of laminar flow, Equation 2, below, can be used to determine D.

$$D=a/(((\Delta P_t V_t-\Delta P_0 V_o)A/M)+b) \qquad \text{Equation 2}$$

where $V_o$ and $V_t$ are the original velocity and the velocity at time t, respectively.

To facilitate real-time determinations of D, the process disclosed above can incorporate a scale 60 contacting the filter 48 or a filter housing 52 to measure particle mass build-up. Care must be taken that pressure lines 28 and 36 be flexible enough so as not to hamper the weighing of the particle build-up. Data lines 62 and 64 connect the flow controller 56 and the scale 60 respectively to a controller readout or computer 66. Alternatively, combining the present invention with an existing real time aerosol mass monitor provides a faster and more sensitive system for measuring, in situ and in real time, the mass accumulated on the filter 48 which in turn allows instant determination of particle MMDs. In situ measurement of M obviates the need for removing the filter in order to measure M and determine D. An exemplary real time mass monitor is the commercially available Tapered Element Oscillating Microbalance (TEOM) particle mass measuring instrument manufactured by Rupprecht and Patashnick, Inc. of Voorheesville, N.Y.

The system 10 may also incorporate an apparatus for determining the chemical composition of the aerosol and/or a radiation monitor monitoring the radiation emitted by the particles accumulated at the filter. If the radioactivity by gram of the aerosol is known one may use the radiation rate to determine the mass accumulated in the filter.

The following variables are considered when using the method to determine aerosol particle diameters:
filter type;
particle type;
the chemical properties of the carrying gas;
gas velocities;

filter cake characteristics; and
minimum and maximum pressure differentials.

Filter Detail

A myriad of filters can be used with the method, depending on particle sizes and flow rates desired. Generally, filters with a high collection efficiency (i.e., in excess of 98 percent) provide good results. High Efficiency Particulate Air (HEPA) filters with efficiencies exceeding 99 percent are particularly suitable. These filters are typically constructed of matted glass or quartz fibers. They are widely used throughout the nuclear industry for the confinement of radioactive aerosols. Several suitable filters are commercially available from suppliers such as Whatnan, Louisa, Va. Generally, pleated filters are sized so that the expected particle cake thickness does not exceed half the spacing between the layers of the filter material.

While filter configurations having a flat surface perpendicular to particle paths are most common, high volume fluted filter types, characterized as accordion-like in structure, can be used when larger flow rates are required. In general, velocities through the filter material of between approximately 0.1 cm/sec and 10 cm/sec can be accommodated with the invented method.

Particle Detail

The invented method and device determine the mass median diameter (MMD) of particles entrained in a carrying medium such as a gas. MMD is defined as the diameter wherein half of the mass of the particles resides in particles with diameters above the MMD and the other half of the mass resides in particles with diameters below the MMD. As such, the method for determining MMD accommodates particles of any shape.

Typical particle diameters to be determined by the invented method and device are at or below approximately 5 $\mu$m, and more particularly, particles ranging from between 0.03 $\mu$m and 5 $\mu$m. This range accommodates the 2.5 $\mu$m particle diameters now designated by the EPA as damaging to lung tissue.

Figure 2:
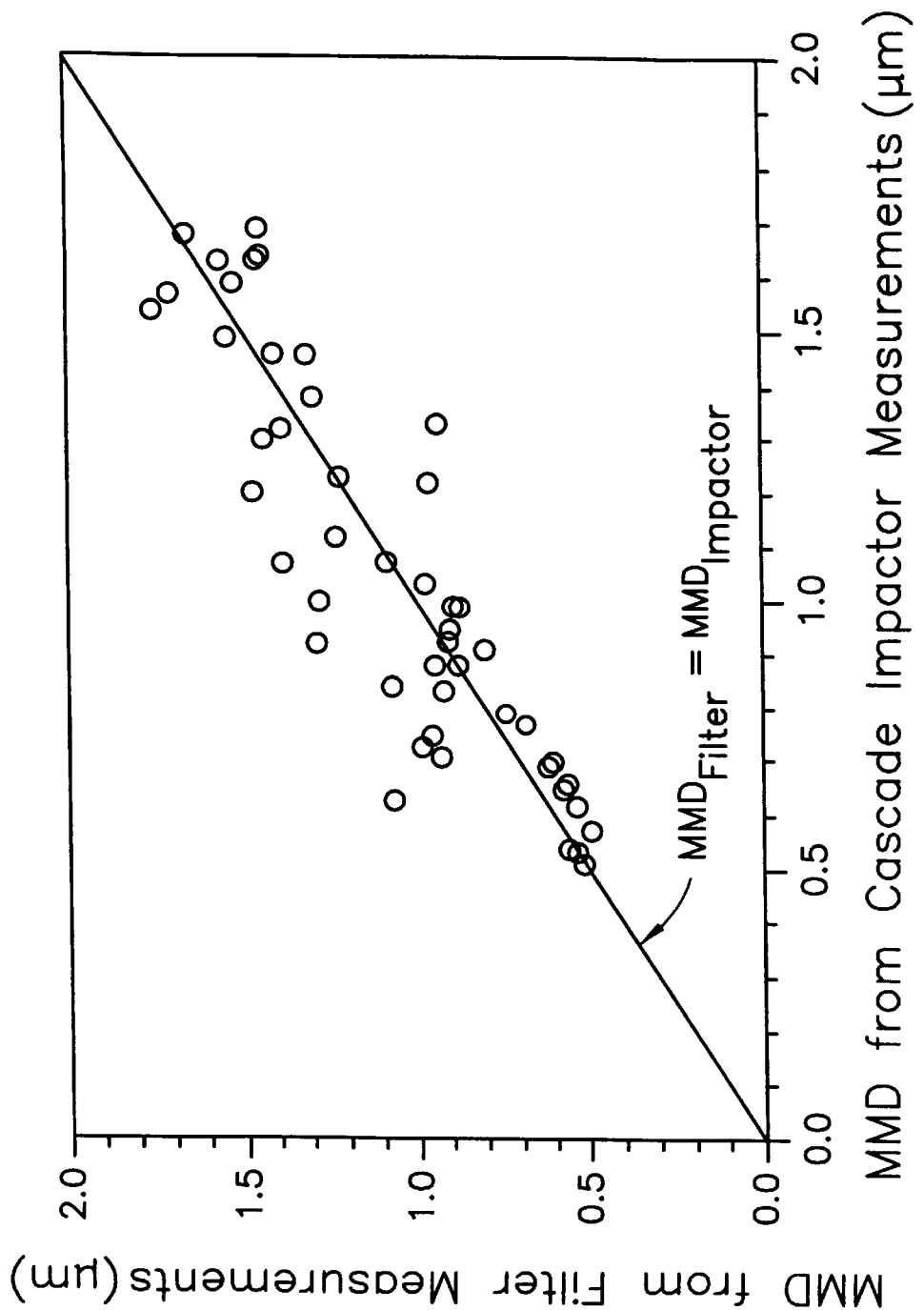

Chemical composition of the aerosols or their mass density are not critical to the process. As depicted in FIG. 2, particle size diameters are determined to within 20 percent of the values determined by a typical prior art diameter measurement system known as a cascade impactor. FIG. 2 illustrates values for NaCl particles (originating from an atomized water solution that was dried), $NH_3Cl$ particles (generated via gas-phase precipitation), and $Al_2O_3$ particles (grinding powder). The diameter measurement of other particle types are facilitated with the method, including but not limited to those particles resulting from metal cutting activities.

Particles which are entrained in a myriad of gases can be measured using the invented method or device. Typical gas includes but is not limited to flue gas, carrier gases, stack gas, and ambient air. Generally, any inert gas (i.e. nitrogen, argon, helium) or any gas that does not react with the particles accumulating on the filter or with the filter itself is suitable.

The various elements of the exemplary embodiment illustrated in FIG. 1 are easily obtained from various suppliers. For example, standard pleated HEPA filters are manufactured by Flanders, Washington, N.C. Flow controllers of the hot wire anemometer variety are available from General Metal Works, Inc., Cleves, Ohio. Capacitance manometers are suitable transducers. Such devices are available from MKS Instruments, Andover, Mass.

While the invention has been described with reference to details of the illustrated embodiment, these details are not intended to limit the scope of the invention as defined in the appended claims.

The embodiment of the invention in which an exclusive property or privilege is claimed is defined as follows:

1. A method for determining the mass median diameter D of particles contained in a fluid and having a total mass M, said method comprising:
   a) passing the fluid maintained at a velocity V through a filter having an area A to determine a first fluid pressure differential $\Delta P_0$ across said filter;
   b) contacting the particles to said filter to retain the particles on said filter;
   c) passing the fluid at the same velocity V through the now-contacted filter to determine a second fluid pressure differential $\Delta P_t$ across said filter and retained particles;
   d) determining the mass M of the retained particles; and
   e) determining the mass median diameter D of the of the particles by means of an equation relating D to $\Delta P_0$, $\Delta P_t$, V, A, and M.

2. The method as recited in claim 1, wherein D is between 0.03 and 5 microns.

3. The method as recited in claim 2, wherein said equation is of the form:

$$D=a/(((\Delta P_t-\Delta P_0)AV/M)+b),$$

wherein a is between 0.9 and 1.0 and b is between $1\times10^5$ and $2\times10$.

4. The method as recited in claim 3 wherein a is 0.95.

5. The method as recited in claim 3 wherein b is $1.6\times10^5$.

6. The method as recited in claim 1, wherein said filter has a collection efficiency in excess of 98%.

7. The method as recited in claim 3 wherein a and b are determined experimentally.

8. The method as recited in claim 1, wherein the fluid is a gas selected from the group consisting of air, noble gases, flue gas, combustion exhaust gases, nitrogen, oxygen, hydrogen, and combinations thereof.

9. The method as recited in claim 1, wherein said particles are solid.

10. The method as recited in claim 1, wherein the pressure differentials $\Delta P_0$ and $\Delta P_t$, are measured by means of a pressure transducer.

11. The method as recited in claim 1, wherein said equation is established empirically by means of an independent device that measures the mass median diameter D of the particles contained in the fluid.

12. The method as recited in claim 1, wherein V is between 0.1 and 10 cm/sec.

13. The method as recited in claim 1 wherein the mass M is measured in situ and the particle size D is determined in real time.

14. A device for determining the mass median diameter D of particles contained in a fluid, said device comprising:
   a) a conduit having a first end and a second end, wherein said first end is adapted to receive the fluid at a first pressure $P_{in}$ and wherein said second end is adapted to exhaust the fluid at a second pressure $P_{out}$;
   b) a filter, with an area A, positioned at a time t=0 between the first and second ends of said conduit with said fluid having a velocity through the filter V at t=0;
   c) pressure probes affixed at each end of the conduit and connected to means for determining a pressure differential $\Delta P_t=P_{in}-P_{out}$ at any time t, with $\Delta P_0$ being the pressure differential at t=0;

d) means for ensuring said fluid has said velocity V when passing through the filter at a predetermined time t by which time t a mass M of particles is collected on the filter;

e) means for measuring V at any time;

f) means for measuring the mass M collected between t=0 and t; and g) means for computing D by means of an equation relating D to $\Delta P_0$, $\Delta P_t$, A, V, and M.

15. The device as recited in claim 14, wherein D is between 0.03 and 5 microns.

16. The device as recited in claim 14, wherein said equation is of the form:

$$D=a/(((\Delta P_t - \Delta P_0)A/VM)+b),$$

wherein a is between 0.9 and 1 and b is between $1 \times 10^5$ and $2 \times 10^5$.

17. The device as recited in claim 16 wherein a is 0.95.

18. The device as recited in claim 16 wherein b is $1.6 \times 10^5$.

19. The device as recited in claim 14, wherein said filter has a collection efficiency in excess of 98%.

20. The device as recited in claim 14, wherein the fluid is a gas selected from the group consisting of air, noble gases, flue gas, combustion exhaust gases, nitrogen, oxygen, hydrogen, carbon dioxide and combinations thereof.

21. The device as recited in claim 14, wherein said particles are solid.

22. The device as recited in claim 14, wherein the pressure differentials $\Delta P_0$ and $\Delta P_t$ are measured by means of a pressure transducer connected to said pressure probes.

23. The device as recited in claim 14, wherein said equation is established empirically by means of an independent device that measures the mass median diameter D of the particles contained in the fluid.

24. The device as recited in claim 14, wherein the fluid velocity V through the filter is between 0.1 and 10 cm/sec.

* * * * *